United States Patent [19]

Malen et al.

[11] 4,283,407

[45] Aug. 11, 1981

[54] THIOPROPIONAMIDES, AND THE PHARMACEUTICAL COMPOSITIONS

[75] Inventors: Charles Malen, Fresnes; Pierre Roger, St. Cloud; Michel Laubie, Vaucresson, all of France

[73] Assignee: Science Union et Cie, Suresnes, France

[21] Appl. No.: 945,253

[22] Filed: Sep. 25, 1978

[30] Foreign Application Priority Data

Sep. 28, 1977 [FR] France ............................ 77 29109
Jan. 6, 1978 [GB] United Kingdom ............. 0051/78

[51] Int. Cl.³ ............... C07D 277/06; A61K 31/425
[52] U.S. Cl. ............................ 424/270; 548/200; 544/54; 544/58.2; 544/58.4
[58] Field of Search ........................ 544/58, 54; 260/306.7 C; 548/201, 200; 424/270

[56] References Cited

U.S. PATENT DOCUMENTS 4,192,878 3/1980 Ondetti .......................... 548/201

FOREIGN PATENT DOCUMENTS 7420M 12/1969 France .
2285876 4/1976 France .
2315271 1/1977 France .

OTHER PUBLICATIONS

Mita et al., Chem. Pharm. Bull, vol. 26, pp. 1333–1335 (1978).

*Primary Examiner*—John M. Ford
*Attorney, Agent, or Firm*—Gordon W. Hueschen

[57] ABSTRACT

This invention relates to omega-mercaptopropionylamides, the nitrogen atom of which is included as a ring atom of a cyclic amino acid.

The application also discloses a process for producing said compounds which comprises reacting an omega-mercaptopropionic acid, or a functional derivative thereof, with a cyclic amino acid.

This invention further relates to pharmaceutical compositions incorporating such an omega-mercaptopropionylamide as active ingredient together with a pharmaceutically-acceptable carrier or vehicle, and a method of employing said compounds.

They find a use in human therapy, namely, as antihypertensive agents.

8 Claims, No Drawings

THIOPROPIONAMIDES, AND THE PHARMACEUTICAL COMPOSITIONS

PRIOR ART

The prior art may be illustrated by the following references:

French Pat. ( to Ital chemi SPA ) No. 2.315.271 Chem.-Pharm.Bulletin 26 ; 1333 ( 1978 )
French Pat. ( to Ludwig Merckle ) No. 2.285.876
French drug Pat. ( to E.R.M.A. ) No. 7420 M

SUMMARY OF THIS INVENTION

This invention provides N ($\omega$-thiopropionyl) cycloalkyl carboxylicacids and their derivatives. These compounds may be illustrated by the following formula:

$$RS-CH_2-CH(R_2)-CON\langle (CH_2)_n-Z, (CH_2)_m, (R_3)_p \rangle COX$$

wherein
R is hydrogen, an acyl radical or a hydrocarbon radical
$R_2$ is hydrogen a lower alkyl or a lower cycloalkyl
$R_3$ is hydrogen or a lower alkyl
and X is a hydroxy or one of the usual derivative of the carboxylic function.

This invention also includes the diastereoisomeric forms and the optically-active isomers.

This invention further includes the base addition salts of these compounds when X is a hydroxy.

This invention also relates to the process for producing said compounds.

This invention still provides pharmaceutical compositions containing as active ingredient (s) at least one of the foregoing compounds and optionally another active ingredient. They are intended for the treatment of hypertension in the man.

DESCRIPTION OF THE PREFERRED EMBODIMENT

This invention provides novel p.ropionamides which are substituted on the alkyl chain with a mercapto group.

More precisely this invention refers to $\omega$-mercapto propionamides having at the nitrogen atom a cyclic subsituent.

Specifically this invention provides $\omega$-mercapto propionamides having the formula I $$R-S-CH_2-CH(R_2)-CO-N\langle (CH_2)_n-Z, (CH_2)_m, (R_3)_p \rangle CO-X \quad (I)$$

wherein
X is a hydroxy, a lower alkoxy or an amino group
R is a hydrogen atom, a lower alkyl radical, a lower alkanoyl radical, an aryl lower alkyl radical or an aryl radical.
$R_2$ is a hydrogen atom, a lower alkyl radical or a lower cycloalkyl radical
$R_3$ is a hydrogen or a lower alkyl radical
Z is a sulphur atom, a sulfoxide $S \to O$ or a sulphonyl—$SO_2$—radical
m is equal to 1 or 2
n the same or different than m is equal to 1 or 2
p is equal to 0,1 or 2

Another object of this invention is to provide the salts of the compounds of formula I with an organic or inorganic base, preferably a therapeutically-compatible base.

The compounds of formula I and the addition salts thereof have at least one asymetric carbon atom and may thus exist in the form of racemic mixtures or as an optically-active compound. Further when the molecule incorporates two asymetric carbon atoms, it is still possible to split the molecule into the two disatereoisomeric forms. The diastereoisomers may further be resolved into their optically-active isomers.

In general the resolution is performed by salification with a chiral base.

The separation of the diastereo isomers and/or the resolution into the optically-active isomers play an imprtant role due to the fact that the pharmacological activity is correlated to the stereo chemistry of the cyclic amino acid moiety. The most active compounds of formula I are those for which the configuration of the carbon atom bearing the carboxylic function is L. When $R_2$ is a lower alkyl radical or a lower cycloalkyl radical the configuration of the carbon atom bearing the said substituent is also of importance for the pharmacological activity.

As far as this invention is concerned the term "lower alkyl" is intended to designate a saturated hydrocarbon chain having from 1 to 6 carbon atoms in straight or branched chain. Examples of such lower alkyl radicals are methyl, ethyl, isopropyl, tertbutyl, sec butyl, neo penty or n hexyl radicals.

The term "lower alkenyl" is intended to designate an unsaturated hydrocarbon chain having from 1 to 3 double bonds and from 2 to 10 carbon atoms. Examples thereof are allyl, methallyl, dimethyl allyl, isopentenyl, but 2-enyl, buta 1,4-dienyl, penta 1,3-dienyl or triallyl methyl.

The term "aryl" is intended to designate a phenyl ring which may be substituted with one to three subsituents selected from the group consisting of halogens, lower alkoxy, trifluoromethyl, lower alkylthio, lower alkylene dioxy, hydroxy and lower alkyl. Examples of such substituted phenyl radicals are 3,4-dimethoxy phenyl, 2,4-dichlorophenyl, m.trifluoromethyl phenyl, 3,4,5-trimethoxyphenyl, 2,6-dimethyl phenyl, 3,5-dimethoxy 4-hydroxyphenyl and the like.

The term "aryl lower alkyl" is intended to designate an aryl radical defined as above, bearing a lower alkyl radical defined as previously.

Examples of such "aryl lower alkyl" radicals are 3,4-dimethoxy benzyl, m.trifluoromethyl benzyl, $\alpha$-methyl benzyl, phenylethyl, phenyl propyl, $\beta$-methyl phenyl ethyl, p.chlorobenzyl, methylenedioxy benzyl and benzyl.

The term "lower cycloalkyl" is intended to designate a saturated hydrocarbonated having from 3 to 6 carbon ring, as cyclopropyl, cyclopentyl or cyclohexyl.

Among the base addition salts of the compounds of formula I they may particularly be cited the salts of the carboxylic function with an inorganic base such as sodium, potassium, lithium, magnesium, strontium, iron (II) or iron (III). They may also be cited base addition salts of the carboxylic function with an organic base such as methylamine, diethyl amine, amino ethanol, phenylethylamine, benzyl amine, dibenzylamine, terbutylamine, dicyclohexylamine, pyridyl methylamine, naphtyl amine, dinaphtylethylenediamine and the like.

The compounds of formula I and the base addition salts thereof are endowed with interesting pharmacological properties. More precisely they are potent inhibit ons of the enzyme which allows the conversion of Angiotensin I into Angiotensin II.

It is known that one of the causes of hypertension is an excessive content of Angiotensin II in the blood. The bio-logical precursor of Angiotensin is Angiotensinogen. The latter is converted by Renin into Angiotensin I which is physiologically inactive, and Angiotensin I is converted into Angiotensin II by a specific carboxypeptidase. The effects of Angiotensin II on blood pressure, especially in hypertensive disease, are of paramount importance and it is of great therapeutic interest to keep normal its level in the blood or to curb its effect on its receptor.

The possibility therefore arise of diminishing or abolishing the effect of Angiotensin II either by selectively inhibiting the conversion of Angiotensin I into Angiotensin II by blocking this enzyme, or by inhibiting the action of Angiotensin II through a competitor for the target site of Angiotensin II.

The possibility also arises of completing or improving the effects of an inhibitor of or a competitor for Angiotensin II with the beneficial effects of a diuretic agent. It is known that the decrease of volhemia resulting from treatment with a diuretic agent induces an increase in the level of plasmatic Renin and consequently a more significant conversion of Angiotensinogen into Angiotensin.

Due to their pharmacological properties they may be cited as preferred compounds, the ω-mercaptopropionamides of formula I'

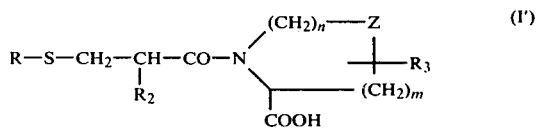 (I')

in which the substituents R, $R_2$, $R_3$, Z, n and m are defined as previously given and specifically N-(3-mercapto 2-methyl propionyl) thiazolidinyl - 4 carboxylic acid and the base addition salts thereof.

N-(3-mercapto 2-methyl propionyl) 1,4-thiazanyl 3-carboxylic acid and the base addition salt thereof.

It may also be cited as interesting compounds:

N-(3-mercapto 2-methyl propionyl) thiazolidinyl-4 carboxamide.

N-(3-mercapto 2-methyl propionyl) 5,5-dimethyl thiazolidinyl carboxylic acid and its dicydohexylamine addition salt.

Methyl N-(3-acetylmercapto 2-methyl propionyl) 2-methylthiazolidinyl - 4 carboxylate.

This invention also provides a process for preparing the compounds of formulas I

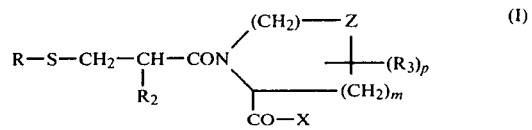 (I)

wherein the substituents R, $R_2$, Z, $R_3$, n, m and p have the above-given definitions which consists in reacting a mercapto propionic acid of the formula II

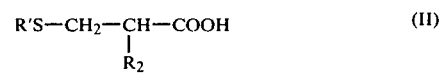 (II)

in which R' is the acyl residue of a lower alkyl carboxylic acid or a triphenylmethyl radical or a functional derivative of the carboxylic function thereof with a lower alkyl ester of a cyclic aminoacid of the formula II

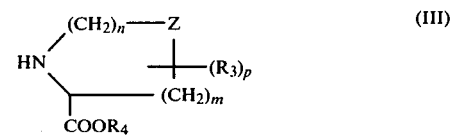 (III)

wherein $R_4$ is a lower alkyl radical

Z' is a sulphur atom and n, m and p have the previously-given definitions to produce a mercapto propionamide of the formula IV

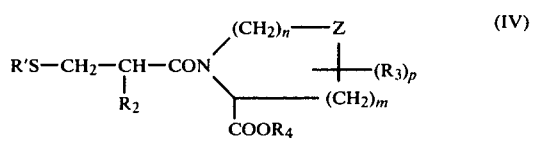 (IV)

wherein the substituent R', $R_2$, $R_3$, $R_4$, n, m and p have the previously given definitions, which may further

*either* partially hydrolysed with a mild reagent to provide the acid of formula V

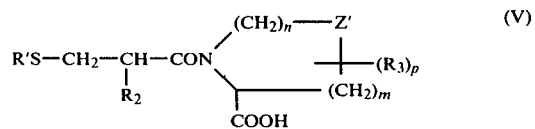 (V)

in which

R' is an acyl residue of a lower alkyl carboxylic acid or a triphenylmethyl radical and $R_2$, $R_3$, Z', n, m and p have the above-given definitions

*either* wholly hydrolysed in astrong basic medium or strong acid medium to produce a mercapto acid of the formula VI $$HS-CH_2-\underset{R_2}{CH}-CON\underset{COOH}{\overset{(CH_2)_n-Z'}{\diagdown}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!-(R_3)_p \atop -(CH_2)_m \qquad (VI)$$

in which

R$_2$, R$_3$, Z', n, m and p have the above definitions
or amidified by reacting it with ammonia to produce a compound of formula VII $$HS-CH_2-\underset{R_2}{CH}-CON\underset{CONH_2}{\overset{(CH_2)_n-Z'}{\diagdown}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!-(R_3)_p \atop -(CH_2)_m \qquad (VII)$$

in which the substituents R$_2$, R$_3$, Z', n, m and p have the above-given definitions.

Further the compounds of formula V may be alkylated, alkenylated, arylated or aryl alkylated by means of an alkylating agent, an alkenylating agent, an arylating agent or an arylakylating agent, namely an halide or a sulphate in basic medium, to produce a compound of formula VIII $$RS-CH_2-\underset{R_2}{CH}-CON\underset{COOH}{\overset{(CH_2)_n-Z'}{\diagdown}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!-(R_3)_p \atop -(CH_2)_m \qquad (VIII)$$

wherein

R is a lower alkyl, a lower alkenyl, an aryl or an aryl lower alkyl radical and R$_2$, Z', R$_3$, n, m and p have the above-given definitions.

It is still possible to convert any compound of formula V, VI, VII or VIII for which Z' is a sulphur atom into a compound of formula I in which Z is a sulfoxide or a sulfone radical by means of a suitable oxydizing agent. Preferably this oxydation step is performed on a compound of formula V.

The compounds of formula V, VI, VII and VIII may also be resolved into their optically-active isomers on split when possible into their diastereoisomers.

The process according to this invention may also be defined by the following features which are presently the preferred ones:

(1) the condensation between the mercaptopropionic acid derivative of formula II or the functional derivative thereof and the lower alkyl ester of the cyclic amino acid of formula III is performed in an inert solvent, preferably a polar solvent as for example tetrahydrofuran, dioxane, pyridine, dimethylsulfoxyde, dimethylacetamide or sulpholane.

(2) Instead of the carboxylic acid of formula II it may be convenient to use a functional derivative such as the chloride, the anhydride, a mixed anhydride or a lower alkyl ester.

(3) The condensation of the carboxylic derivative of formula III may be performed in the presence of an activator of the carboxylic function such as a dilower alkyl - or dicycloalkylcarbonyldi-imide, a carbonyldiimidazole or ethoxy acetylene.

This condensation may also be performed in the presence of a promoter such as 4-dimethylamino pyridine or 4-pyrrolidino pyridine.

(4) The partial hydrolysis of a compound of formula V is performed either in mild acidic medium when R' is an acyl residue of a lower alkyl carboxylic acid or in mild basic medium when R' is triphenylmethyl radical.

(5) The total hydrolysis is performed in a strong basic medium preferably using a strong mineral base such as sodium hydroxyde or potassium hydroxyde.

(6) the oxydation of the sulphur atom into a sulfoxyle is performed using a mild oxydizing agent such as a peroxyde for example hydrogen peroxyde, benzoyl peroxyde, hexafluoroacetone peroxyde ; a N-oxyde of a nitrile such as benzonitrile N-oxyde ; a peracid such as perphtalic acid or p.nitro perbenzoic acid.

(7) The oxydation of the sulphur atom into a sulphonyl group occurs using a strong oxydizing agent such as potassium permanganate or the complex chromic anhydride - pyridine.

(8) The separation of the diastereoisomers is performed using the conventional methods, namely vapor phase chromatography, high pressure liquid phase chromatography (HPLC) or thin-layer chromatography (TLC).

(9) The resolution of the optically-active isomer, is performed when X is a hydroxyl using a chiral base such as ephedrine, bruoine, sparteine, 1-p.nitrophenyl 2-amino propane diol (erythro or threo isomers), d-glucosamine or N-methyl d-glucamine.

This resolution may also be performed from compounds for which X is a lower alkyl radical or an amino radical by means of an optically-active acid such as dibenzoyl tartaric acid.

This invention also provides pharmaceutical compositions containing as active ingredient at least one compound of formula I, an optically-active isomer or a diastereoisomeric form thereof or a base addition salt thereof in admixture or conjunction aith an inert non-toxic pharmaceutically-acceptable carrier or vehicle.

The present invention also seeks to provide compositions which produce both a decrease in the content of Angiotensin II in the blood and an increase of diuresis and/or peripheral vasodilatation.

In accordance with the present invention, there are provided anti-hypertensive pharmaceutical compositions comprising as active ingredients an inhibitor for the enzyme which is responsible for the conversion of Angiotensin I into Angiotensin II, and a diuretic agent and/or a peripheral vasodilatator.

The therapeutic effects of both active ingredients appears to be complementary and the resulting effect is better than the additive effect of each active ingredient taken alone in the treatment of hypertension.

The diuretic agent may be defined as a therapeutic agent which has an inhibitory action on tubular reabsorption from an external or internal basis. It may be saliuretic agent, a derivative of ethacrinic acid or their analogues. More especially the diuretic agent is a benzothiadiazine derivative, for example a thiazide or dihydrothiazide, a benzenesulphonamide, a derivative of phenoxyacetic acid, a derivative of benzofuran-2-carboxylic acid, or a derivative of 2,3-dihydrobenzofuran-2-carboxylic acid.

By "thiazide" there is to be understood a compound of the formula

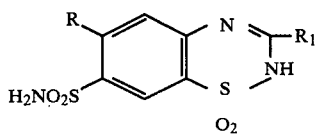

in which
R₁ is a hydrogen atom or a phenyl (lower alkyl)-thio-lower alkyl group; and
R is a halogen atom or a trifluoromethyl group, for example 6-chloro-7-sulphamoyl-1,2,4-benzothiadiazine-1,1-dioxide, 6-trifluoromethyl-7-sulphamoyl-1,2,4-benzothiadiazine-1,1-dioxide and 2-benzylthiomethyl-6-chloro-7-sulphamoyl-1,2,4-benzothiadiazine-1,1-dioxide.

By "hydrothiazide" there is to be understood a compound of the formula

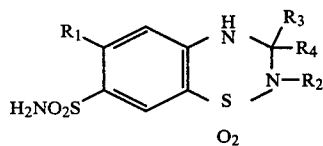

in which
R₂ is a hydrogen atom or a lower alkyl group;
R₃ is a hydrogen atom or a lower alkyl, lower alkenyl, lower cycloalkyl, lower cycloalkenyl, lower cycloalkyl-lower alkyl, aryl, aryl-lower alkyl, lower haloalkyl, lower alkylthio-lower alkyl, lower alkenylthio-lower alkyl, halo-lower alkylthio-lower alkyl, phenyl-lower alkylthio-lower alkyl or heterocyclyl-lower alkyl group;
R₄ is a hydrogen atom or together with R₃ forms a lower alkylene group; and
R₁ is a halogen atom or a trifluoromethyl group, for example 3-ethyl-6-chloro-7-sulphamoyl-3,4-dihydro-1,2,4-benzo thiadiazine-1,1-dioxide; 3-trichloromethyl-6-chloro-7-sulphamoyl-3,4-dihydro-1,2,4-benzothiadiazine-1,1-dioxide; 3-benzyl-6-trifluoromethyl-7-sulphamoyl-3,4-dihydro-1,2,4-benzothiadiazine-1,1-dioxide; 2-methyl-3-(2,2,2-trifluoroethylthiomethyl)-6-chloro-7-sulphamoyl-3,4-dihydro-1,2,4-benzothiadiazine-1,1-dioxide; 3-(2,2,2-trifluoroethylthiomethyl)-6-chloro-7-sulphamoyl-3,4-dihydro-1,2,4-benzothiadiazine-1,1-dioxide; 3-(5-norbornen-2-yl)-6-chloro-7-sulphamoyl-3,4-dihydro-1,2,4-benzothiadiazine-1,1-dioxide; 2-methyl-3-chloromethyl-6-chloro-7-sulphamoyl-3,4-dihydro-1,2,4-benzothiadiazine-1,1-dioxide; 6-chloro-7-sulphamoyl-3,4-dihydro-1,2,4-benzothiadiazine-1,1-dioxide; 3-dichloromethyl-6-chloro-7-sulphamoyl-3,4-dihydro-1,2,4-benzothiadiazine-1,1-dioxide; 3-cyclopentylmethyl-6-chloro-7-sulphamoyl-3,4-dihydro-1,2,4-benzothiadiazine-1,1-dioxide; 6-trifluoromethyl-7-sulphamoyl-3,4-dihydro-1,2,4-benzothiadiazine-1,1-dioxide and 3-isobutyl-6-chloro-7-sulphamoyl-3,4-dihydro-1,2,4-benzothiadiazine-1,1-dioxide.

By "sulphamide", there is to be understood a compound of the formula

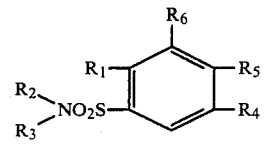

in which
R₁ is a halogen atom or a lower alkyl or trifluoromethyl group;
R₂ is a hydrogen atom or a lower alkyl or phenyl-lower alkyl group, a phenyl-lower alkyl group the phenyl ring of which may carry one or more substituents selected from halogen atoms and lower alkoxy and amino groups, or a pyrrolidinomethyl, piperidinomethyl, piperazinomethyl, morpholinomethyl or thiamorpholinomethyl group;
R₃ is a hydrogen atom or a lower alkyl group;
R₄ is a carboxyl, carbamoyl, monosubstituted carbamoyl, disubstituted carbamoyl, lower alkyl-sulphonyl, piperidinosulphonyl, sulphamoyl, monosubstituted sulphamoyl, disubstituted sulphamoyl, furfurylamino-sulphonyl, tetrahydrofurfurylamino-sulphonyl, (N-lower alkyl-N-[2-methyl-tetrahydrofurfuryl]-amino)-sulphonyl, (N-lower alkyl-N-[2-methyl-4-oxo-tetrahydrofurfuryl]-amino)-sulphonyl, 1- or 3-isoindolinyl (which may be oxo- and/or hydroxy-substituted), indolyl-1-aminocarbonyl, (2-lower alkyl-indolyl-1)-aminocarbonyl, (2-lower alkyl-indolinyl-aminocarbonyl or (di-lower alkyl-piperidino)-aminocarbony group;
R₅ is a hydrogen atom or a lower alkyl, amino, lower alkylamino, di-lower alkylamino, tetrahydrofurfurylamino, furfurylamino, benzylamino or dibenzylamino group;
or R₄ and R₅ together with the phenyl ring to which they are attached, form 4-oxo-3-(o-tolyl)-2-methylquinazoline, 1-oxo-2-cyclohexylisoindoline or 4-oxo-2-ethylquinazoline;
and R₆ is a hydrogen or halogen atom, especially 2-chloro-5-methylsulphonamido-benzene-sulphonamide, 2-chloro-5-dimethylsulphonamido-benzene-sulphonamide, 2-chloro-5-piperidinosulphonyl-benzene-sulphonamide, 2-chloro-5-(N-carboxymethyl-N-methylsulphonamido)-benzene-sulphonamide, 2-chloro-5-furfurylsulphonamido-benzene-sulphonamide, 2-chloro-5-tetrahydrofurfurylsulphonamido-benzene-sulphonamide, 2-chloro-5-(N-methyl-N-[2-methyl-4-oxo-tetrahydrofurfuryl]-sulphonamido)-benzenesulphonamide, 4,5-dichlorobenzene-1,3-disulphonamide, 4-chloro-6-methyl-benzene-1,3-disulphonamide, 4-chloro-6-aminobenzene-1,3-disulphonamide, 2-chloro-5-methylsulphonyl-benzene-sulphonamide, 2-chloro-5-ethylsulphonyl-benzene-sulphonamide, 2-chloro-5-n-butylsulphonyl-benzene-sulphonamide, 2-methyl-5-ethylsulphonyl-benzene-sulphonamide, 2-methyl-5-methylsulphonylbenzene-sulphonamide, 2-methyl-5-n-butyl-sulphonyl-benzenesulphonamide, 2-chloro-4-dibenzylamino-5-carboxybenzenesulphonamide, 2-furfurylamino-4-chloro-5-N-(p-aminophenyl)-sulphamoyl-benzoic acid, 2-furfurylamino-4-chloro-5-N-(o-aminophenyl)-sulphamoyl-benzoic acid, 3-sulphamoyl-4-chlorobenzoic acid, 3-sulphamoyl-4-chloro-benzamide, 3-methylsulphamoyl-4-chloro-N-methylbenzamide, 1-chloro-4-[N-methyl-N(2-methyltetrahydrofurfuryl)-sulphamoyl]-benzene-sulphonamide, 1,3-disulphamoyl-4-chlorobenzene, 2-chloro-5-[3-hydroxy-1-oxo-isoindolinyl-(3)] benzene-sulphonamide, 2-ethyl-4-oxo-6-sulphamoyl-7-chloro-1,2,3,4-tetrahydro-quinazoline, 1-oxo-2-cyclohexyl-5-chloro-6-sulphamoyl-isoindoline, 2-chloro-5-]N-(2,6-dimethylpiperidino)-carbamoyl] benzosulphonamide, 2-chloro-4-furfurylamino-5-carboxybenzene-sulphonamide, 2-chloro-4-benzylamino-5-carboxy-benzene-sulphonamide and N-(3'-sulphamoyl-4'-chlorobenzamido)-2-methyl-indoline.

By "a derivative of phenoxy acetic acid" there is to be understood a compound of the formula

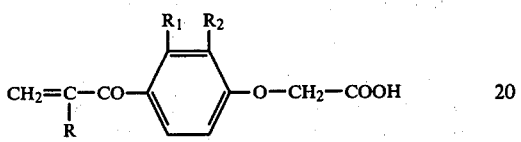

in which

R is a lower alkyl group;
$R_1$ is a halogen atom or a lower alkyl group;
$R_2$ is a hydrogen or halogen atom or a lower alkyl group;
or $R_1$ and $R_2$ together form a lower alkylene or a buta-1,3-dienylene group, for example [2,3-dimethyl-4-(2-methylene-butyryl)-phenoxy]-acetic acid; [2-methyl-3-chloro-4-(2-methylene-butyryl)-phenoxy]-acetic acid; [4-(2-methylenebutyryl)-1-naphthoxy]-acetic acid and [2,3-dichloro-4-(2-methylene-butyryl)-phenoxy]-acetic acid.

Another phenoxy-acetic acid derivative which may be used is 2,3-dichloro-4-(thenyl-2-carbonyl)-phenoxy acetic acid.

By "a derivative of benzofuran-2-carboxylic acid" there is to be understood a compound of the formula

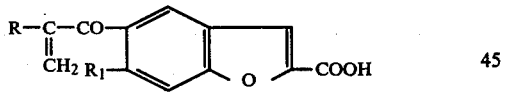

in which

R is a lower alkyl group; and
$R_1$ is a lower alkyl or a lower alkoxy group, for example 5-(2-methylene-butyryl)-6-methyl-benzofuran-2-carboxylic acid; 5-(2-methylene-butyryl)-6-methoxy-benzofuran 2-carboxylic acid and 5-(2-methylene-propionyl)-6-methylbenzofuran-2-carboxylic acid.

By "a derivative of 2,3-dihydrobenzofuran-2-carboxylic acid", there is to be understood a compound of the formula

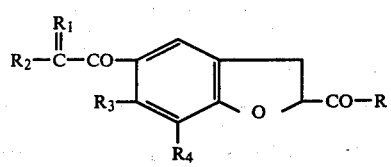

in which

R is a hydroxy group, an alkoxy group having up to 12 carbon atoms, or a lower cycloalkyloxy or aryl-lower alkoxy group;
$R_1$ is two hydrogen atoms or a lower alkylidene group;
$R_2$ is a lower alkyl group;
$R_3$ is a hydrogen or halogen atom or a lower alkyl or lower alkoxy group; and
$R_4$ is a hydrogen atom or a lower alkyl group, for example 5-(2-methylene-butyryl)-6-methyl-2,3-dihydro-benzofuran-2-carboxylic acid, 5-(2-methylene-butyryl)-6-fluoro-2,3-dihydrobenzofuran-2-carboxylic acid, 5-(2-methylene-butyryl)-6-chloro-2,3-dihydrobenzofuran-2-carboxylic acid, 5-(2-methylene-propionyl)-6-methyl-2,3-dihydrobenzofuran-2-carboxylic acid, 5-(2-methylene-hexanoyl)-6-methyl-2,3-dihydrobenzofuran-2-carboxylic acid, 5-(2-methylene-valeryl)-6-methyl-2,3-dihydrobenzofuran-2-carboxylic acid, 5-(2-methylenepropionyl)-6methyl-2,3-dihydrobenzofuran-2-carboxylic acid, 5-(2-ethylidene-butyryl)-6-methyl-2,3-dihydrobenzofuran-2-carboxylic acid, methyl 2-(methylene-butyryl)-6-methyl-2,3-dihydrobenzofuran-2-carboxylate, ethyl 5-(2-methylene-butyryl)-6-methyl-2,3-dihydrobenzofuran-2-carboxylate, n-butyl 5-(2-methylene-butyryl)-6-methyl-2,3-dihydrobenzofuran-2-carboxylate, 2-hexyl 5-(2-methylene-butyryl)-6-methyl-2,3-dihydrobenzofuran-2-carboxylate, n-decyl 5-(2-methylene-butyryl)-6-methyl-2,3-dihydrobenzofuran-2-carboxylate, cyclopentyl 5-(2-methylene-butyryl)-6-methyl-2,3-dihydrobenzofuran-2-carboxylate, cyclohexyl 5-(2-methylene-butyryl)-6-methyl-2,3-dihydrobenzofuran-2-carboxylate, benzyl 5-(2-methylene-butyryl)-6-methyl-2,3-dihydrobenzofuran-2-carboxylate, methyl 5-(2-methylene-butyryl)-7-methyl-2,3-dihydrobenzofuran-2-carboxylate, methyl 5-(2-methylene-butyryl)-6-chloro-7-methyl-2,3-dihydrobenzofuran-2-carboxylate, methyl 5-(2-methylenepropionyl)-6-methyl-2,3-dihydrobenzofuran-2carboxylate, methyl 5-(2-methylene-valeryl)-6-methyl-2,3-dihydrobenzofuran-2-carboxylate, methyl 5-(2-methylene-3-methylbutyryl)-6-methyl-2,3-dihydrobenzofuran-2-carboxylate and methyl 5-(2-methylene-butyryl)-6-fluoro-2,3-dihydrobenzofuran-2-carboxylate.

The present invention also provides pharmaceutical compositions comprising as active ingredients either an inhibitor for the enzyme which is responsible for converting Angiotensin and a peripheral vasodilatator. The peripheral dilatator may be, for example Piribedil; Minoxidil; an imidazoline derivative, for example 2-benzyl-4,5-imidazoline; a sympathetic tonus depressant, for example N-o-bromobenzyl-N-ethyl-N,N-dimethylammonium p-toluenesulphonate; a derivative of a substituted guanidine, for example 7-bromo-1,2,3,4-tetrahydro-isoquinolinyl-2-carboxamidine, 1-benzyl-2,3-dimethylguanidine, and $\beta$-(1-azacyclooctyl)-ethylguanidine; a hydrazinopyridazine, for example hydrazinophthalazine, 1,4-dihydro-hydrazinophthalazine; or a polynitro derivative, for example trinitroglycerol, tetranitropentaerythritol and hexanitro-meso-inositol.

Preferred pharmaceutical compositions according to the present invention are those which contain as active ingredients an inhibitor for the enzyme which is responsible for converting Angiotensin I into Angiotensin II, selected from N-(3-mercapto-2-methylpropionyl)- thiazolidinyl-4-carboxylic acid and its dicyclohexylamine addition salt and N-(3-mercapto-2-methyl-propionyl) -1,4-thiazanyl 3-carboxylic acid and its dicyclohexylamine addition salt, together with either N-(4'-chloro-3'-sulphamidobenzoyl)-2-methyl-indoline, or Piribedil, or Minoxidil, orl, 4-dihydrohydrazinophthalazine, or trinitro-glycerol.

The pharmaceutical compositions according to the present invention are preferably in a form suitable for parenteral, oral, rectal or sublingual administration. They may include a pharmaceutically suitable carrier, for example a diluent, binder, filling agent or other vehicle appropriate for a particular method of administration.

The compositions are most preferably in the form of injectible solutions or suspensions, for intravenous perfusion; or an orally acceptable form such as tablets or soft gelatine capsules.

The active ingredients may be intravenously administered at doses ranging from 10 to 20 pg/minute. For intravenous administration, the efficacious dose of enzyme inhibitor is about 30pg/Kg. The duration of the effect is about 3 to 4 hours.

When used orally the compounds of formula I alone or together with a diuretic or peripheral vasodilatator, are used in the form of pharmaceutical compositions containing from 10 to 100 mg of a compound of formula I or a salt thereof. They may be administered from 1 to 3 times a day.

This invention further includes a method for treating hypertension in hypertensive patients suffering from an excessive blood content of Angiotensin II which consists in administering to said patients an amount of a compound of formula I or a salt thereof alone or in admixture with a diuretic or a peripheral vasodilatator, efficient to curb the conversion into Angiotensine II.

The daily dosage ranges from 20 to 100 mg per day of a compound of claim 1. The daily dosage of the diuretic ranges from 5 mg to 7.5 mg depending of the nature of the diuretic compound.

The daily dosage of the peripheral vasodilatator may range from about 0.05 to 0.20 g.

The following examples illustrate this invention. They do not limit it in any manner.

The starting material of formula II are easily obtained by reacting a thio-acid with an unsubstituted or substituted acrylic acid according to the method described by SN Lewis and Cowork. J. Heterocyclic chem 8 571–580.

The cyclic amino acids are known material. They are either from natural olefin or obtained by condensing a carbonylated derivative with a ω-thio amino acid such a cysteine, homocysteine and the like. They may also be obtained by condensing a lower alkyl amino-thiol with an ester of an αβ-dihalogeno lower alkyl carboxylic acid.

EXAMPLE I

N(2-methyl 3-mercaptopropionyl) thiazolidinyl-4 carboxylic acid and its dicyclohexylamine addition salt (mixture of epimers α and β)

Step A

In a three-neck flask they are successively introduced 5.9 g of methyl L-thiazolidinyl 4-carboxylate, 40 ml benzene and 5.5 ml triethyl amine. After complete dissolution 7.2 g 3-acetyl thio 2-methyl propionic acid chloride previously dissolved in 20 mg benzene are slowly added while maintaining the inner temperature below 20°.

The addition takes about 1 hour and it appears progressively a gelatinous precipitate of triethylamine hydrochloride. The mixture is kept aside for a further, one hour washed with water until the washings are freed of chloride ions. The benzenic phase is then dried on sodium sulphate, filtered and the solvent is evaporated off under reduced pressure—11 g of an oily residue is recovered which is used without further purification for the next step of the synthesis.

Step B 8.8 g of raw methyl N-(2-methyl 3-acetyl mercapto propionyl) L-thiazolidinyl - 4 carboxylate are dissolved in 90 ml ethanol and 90 ml of a N aqueous solution of sodium hydroxyle is added thereto. The whole mixture is kept under stirring for a night at room temperature under inert gas.

The mixture is then evaporated to half volume under reduced pressure. The clear solution is extracted three times with ether then acidified until pH 2 by adding hydrochloric acid. It appears a water-insoluble phase which is extracted with ether. The organic solutions are united, whashed with water, dried, filtered and evaporated off.

6 g of N(3-mercapto 2-methylpropionyl) L-thiazolidinyl - 4 carboxylic acid are thus obtained.

The purity of the product is ascertained by protometric titration in anhydrous medium Infra-red spectrum Presence of stretchings between 3700 cm and 2300 cm $^{-1}$ due to the OH and SH bands.

Presence of a broad absorption at 1720 cm$^{-1}$ (carbonyl of the carboxylic function) and at 1600 cm$^{-1}$ (carbonyl of the amide function)

Rotary power (c=1% benzene).

| $\chi$ | $[\alpha]^{25}$ |
|---|---|
| 578 m | −85.6 |
| 546 m | −98 |
| 436 m | −174.2 |
| 365 m | −289.5 |

This acid is converted into its dicyclohexylamine salt which melts at 160 then 175°. It is very soluble in water. The pH of the aqueous solution ranges between 6 and 7.

| Analysis: $C_8 H_{13} NO_3S_2$, $C_{12} H_{23} N$ = 416,61 | | | | |
|---|---|---|---|---|
| | C | H | N | S % |
| Calculated | 57.66 | 8.71 | 6.72 | 15.40 |
| Found | 57.92 | 8.45 | 6.49 | 15.39 |

Rotary power : c=1% ethanol.

| $\chi$ | $[\alpha]^{25}$ |
|---|---|
| 578 m | −77°4 |
| 546 m | −88°8 |
| 436 m | −159°7 |
| 365 m | −270°6 |

3-acetylthio 2-methyl propionic acid chloride is obtained according to the method described by Daenniker Helv. Chim. Acta 40 (1907) 2148.

Methyl L-thiazolidinyl - 4 carboxylate is obtained according to the method described by Ratnor J of Am Chem. Soc 59 (1937) 200.

EXAMPLE II

N (3-mercapto 2-methyl propionyl) 1,4-thiazanyl -3carboxylic acid

Step A 4.7 g ethyl dl 1,4-thiazanyl - 3 carboxylate are dissolved in 30 ml benzene and 2.7 g of triethylamine are added thereto. The mixture is cooled to 0° in a mixture of water and ice, then a solution of 4.9 g of 3-acetylthio 2-methyl propionic acid chloride in 15 ml benzene is added thereto in about 30 mn. The whole mixture is kept under stirring and cooling for a night. The mixture is thereafter washed with water to dissolve the insoluble matters. The benzenic phase is separated, washed again with water, dried, filtered and evaporated off. The resulting oily residue weighing 8.6 g is essentially formed of ethyl N-(3-acetyl thio 2-methyl propionyl) 1,4-thiazanyl - 3 carboxylate.

Step B

Using the same procedure as in example I step B starting from 7.7 g of ethyl N-ethyl (3-acethylthio 2-methyl propanoyl) 1,4-thiazanyl 3-carboxylate, 5.2 g of (3-mercapto 2-methyl propionyl) 1,4-thiazanyl - 3 carboxylic acid are obtained.

NMR spectrum:

In accordance with the structure.

Absence of vibrations due to the group $SCOCH_3$.

IR spectrum:

Broad absorption at about 1730 cm$^{-1}$ (carbonyl of the carboxylic function).

Very broad absorption at about 1630 cm$^{-1}$ (carbonyl of the amide function).

Absorption at 3700 cm$^{-1}$ and 2300 cm$^{-1}$ (hydroxy and thiol functions).

This acid may be converted into the dicyclohexylamine salt which melts at 146°-150°, by TLC the dicyclohexylamine salt appears to be homogeneous.

NMR spectrum in accordance with the structure.

EXAMPLE III

N-(3-mercapto 2-methylpropionyl) thiazolidinyl 4-carboxamide (mixture of epimers)

Starting from 3.2 g methyl N-(3-acetylmercapto 2-methyl propionyl) thiazolidinyl 4-carboxylate dissolved in 45 ml ethanol and 10 ml strong ammonia and refluxing the mixture of 1 hour, raw N-(3-mercapto 2-methyl propionyl) thiazolidinyl - 4 carboxamide is obtained.

The compound is further purified by dissolving it in hot water and letting the mixture in cool place for a night. The resulting precipitate is separated by succion-filtration, washed with water saturated with ether and dried.

(3-mercapto 2-methyl propionyl) thiazolidinyl-4 carboxamide appears as colourless microcrystalls, sparingly soluble in water. It does not show any clear melting zone.

| Analysis: $C_8 H_{14} N_2 O_2 S_2$ = 234.34 | | | | |
| --- | --- | --- | --- | --- |
| | C | H | N | S % |
| Calculated | 41.01 | 6.02 | 11.95 | 27.37 |
| Found | 40.88 | 6.02 | 11.58 | 27.41 |

The title compound may also be obtained by condensing thiazolidinyl-4 carboxamide with 3-acethio 2-methyl propionyl chloride. The resulting thioacetate is further saponified into N(3-mercapto 2-methyl (propionyl) thiazolidinyl 4-carboxamide by means of an aqueous sodium hydroxyde solution.

The resulting compound has about the same analytical data than the compound obtained by the other way.

EXAMPLE IV

N-(2-methyl 3-mercapto propionyl) 5,5-dimethyl thiazolidinyl 4-carboxylic acid and its dicyclohexylammonium salt (mixtures of epimers)

Using the same procedure as in example I and starting from methyl d-5,5-dimethyl thiazolidinyl 4-carboxylate, they are successively obtained.

Methyl N-(3-acetylthio 2-methyl propionyl) d-5,5 dimethyl thiazolidinyl 4-carboxylate.

-N-(3-mercapto 2-methyl propionyl) d-5,5-dimethyl thiazolidinyl 4-carboxylic acid.

the dicyclohexylammonium salt

Melting at 151°-160°.

Soluble in water.

| Analysis: 263.39 + 181.31 = 444.70 | | | | |
| --- | --- | --- | --- | --- |
| | C | H | N | S % |
| Calculated | 59.42 | 9.07 | 6.30 | 14.42 |
| Found | 59.33 | 8.98 | 6.29 | 14.57 |

Rotatory power (c=1% water).

| λ | $[\alpha]_{25}$ |
| --- | --- |
| 578 | +18° |
| 546 | +20.7° |
| 436 | +38.8° |
| 365 | +69° |

The starting material methyl d-5,5-dimethyl thiazolidinyl 4-carboxylate is prepared from d-penicillamine by cyclization with formaldehyde then esterification with diazomethane into the methyl ester.

EXAMPLE V

N-(2-methyl 3-mercapto propionyl) 2-methyl thiazolidinyl 4-carboxylic acid (mixture of diastereoisomers)

Using the same procedure as in example I and starting from methyl 2-methylthiazolidinyl 4-carboxylate, they are successively obtained:

Methyl N-(2-methyl 3-acetyl mercapto propionyl) 2-methyl thiazolidinyl 4-carboxylate as a colourless liquid.

| Analysis: $C_{12} H_{19} N O_4 S_2$ = 305.41 | | | | |
| --- | --- | --- | --- | --- |
| | C | H | N | S % |
| Calculated | 47.18 | 6.27 | 4.58 | 20.99 |
| Found | 47.09 | 6.36 | 4.86 | 20.71 |

Rotary power (c:1% ethanol).

| λ | $[\alpha]_{24}$ |
| --- | --- |
| 578 | −96.7° |
| 546 | −111.4° |
| 436 | −204,5° |

-continued

| λ | $[\alpha]_{24}$ |
|---|---|
| 365 | −356.5° |

N-(2-methyl 3-mercapto propionyl) 2-methyl thiazolidinyl 4-carboxylic acid (mixture of diastereoisomers) melting at 164°–170°.

Its tertbutylammonium salt is very soluble in water. The aqueous solution is neutral.

EXAMPLE VI

N-(3-mercapto 2-methyl propionyl) 5,5-dimethyl thiazolidinyl 4-carboxylic, acid and its dicyclohexyl ammonium salt (mixture of isomers)

Using the same procedure as in example IV but starting from methyl dl 5,5-dimethylthiazolidinyl 4-carboxylate (obtained from dl 3,3-dimethylcysteine), N-(3-mercapto 2-methyl propionyl) 5,5-dimethyl thiazolidinyl 4-carboxylic acid is obtained.

Its dicyclohexylammonium salt melts at 178°–182°. Its dissolves in water only by warming.

Analysis: $C_{10}H_{17}NO_3S_2 + C_{12}H_{23}N = 444,69$

|  | C | H | N | S % |
|---|---|---|---|---|
| Calculated | 59.42 | 9.07 | 6.30 | 14.42 |
| Found | 59.41 | 8.86 | 6.11 | 14.57 |

EXAMPLE VII

N-(D-3-mercapto 2-methylpropionyl) L-thiazolidinyl 4-carboxylic acid and its tertbutylammonium salt.

Using the same procedure as in example I and starting from dl 3-mercapto 2-methyl propionyl chloride and thiazolidinyl -4 carboxylic acid (laevorotatory) in a mixture of triethylamine and dimethyl formamide, N-(3acetylthio 2-methyl propionyl) L-thiazolidinyl 4-carboxylic acid is obtained. The latter is resolved into its optically-active isomers using a chiral base such as l-ephedrine-N-(D-3-acetylthio 2-methyl propionyl) L. Thiazolidinyl 4-carboxylic acid is thus obtained.

By saponifying it by means of an aqueous solution of sodium hydroxyde N-(D-3-mercapto 2.methyl propionyl) L.thiazolidinyl 4-carboxylic acid is obtained and converted into its tertbutylammonium salt.

This salt is very soluble in water.
Melting point 134°–147°.

Analysis: $C_8H_{13}NO_3S_2 \cdot C_4H_{11}N = 308.44$

|  | C | H | N | S % |
|---|---|---|---|---|
| Calculated | 46.72 | 7.84 | 9.08 | 20.79 |
| Found | 46.78 | 7.95 | 8.92 | 20.74 |

Rotatory power (c=1% ethanol).

| λ | $[\alpha]_{26}$ |
|---|---|
| 578 mμ | −147.2° |
| 546 mμ | −169.3° |
| 436 mμ | −303.1° |
| 365 mμ | −515.2° |

EXAMPLE VIII

Injectible solution for intravenous perfusion

| N-(3-mercapto 2-methylpropionyl) thiazolidinyl-4-carboxylic acid, dicyclohexylammonium salt | .015 g |
|---|---|
| N-(3′-sulfamoyl 4-chlorobenzamido) 2-methyl Indoline | .075 g |
| methyl p.hydroxybenzoate | .15 g |
| propyl p.hydroxybenzoate | .15 g |
| lithium chloride | 6.5 g |
| sterile water enough for | 1 liter |

EXAMPLE IX

Injectible solution for intravenous perfusion

| N-(3-mercapto 2-methyl propionyl) thiazolidinyl 4-carboxylic acid, dicyclohexylammonium salt | .015 g |
|---|---|
| piribedil monomethane sulphonate | .060 g |
| phenylmercury nitrate | .015 g |
| lithium chloride | 6.5 g |
| sterile water enough for | 1 liter |

EXAMPLE X

Tablets containing 10 mg active ingredient each

| N-(3-mercapto 2-methyl propionyl) thiazolidinyl 4-carboxylic acid | 10 g |
|---|---|
| Minoxidil | 20 g |
| calcium phosphate | 75 g |
| kaolin | 125 g |
| corn starch | 15 g |
| polyvinyl poly pyrrolidone (sold under the trade Name Polyclar AT) | 30 g |
| for 1000 tablets weighing each about | .25 g |

EXAMPLE XI

Tablets containing 15 mg active ingredient each

| N-(3-mercapto 2-methylpropionyl) 5,5-dimethyl thiazolidinyl 4-carboxylic acid, dicyclohexylammonium salt | 25 g |
|---|---|
| 5-aminosulphamoyl 4-chloro 2-(2-furanyl methylamino) benzoic acid | 45 g |
| Corn starch | 70 g |
| Mais starch | 60 g |
| Formolated Casein | 20 g |
| Magnesium stearate | 15 g |
| Talc | 15 g |
| for 1000 tablets weighing each about | .25 g |

EXAMPLE XII

Tablets containing 10 mg active ingredient

| N-(D-2-mercapto 2-methyl propionyl) L-Thiazolidinyl 4-carboxylic acid as the tertbutylammonium salt | 13.1 | g |
|---|---|---|
| calcium phosphate | 125 | g |
| corn starch | 35 | g |
| carboxymethyl starch | 25 | g |
| formolated casein | 5 | g |
| colloidal silica | 5 | g |
| magnesium silicate | 25 | g |
| talc | 25 | g |
| for 1000 tablets weighing each about | 25 | g |

EXAMPLE XIII

Pharmacological study of the compounds of formula I

Inhibition of vasopressor response to angiotensin I in anaesthetized dogs.

Methods

Mongrel dogs were anaesthetized with chloralose (100 mg/KG i.v.) and ventilated with a Mark VII Bird Respirator. Blood pressure was recorded on a brusch 400 recorder with a casheter introduced into the aorta via the femoral artery and connected to a Statham P23 Db transducer.

Angiotensin I and angiotensin II were injected intravenously. Three point dose-response curves to angiotensin I and angiotensin II were obtained. The compounds were injected intravenously and a second three-point dose-response curve to angiotensin I and angiotensin II were obtained 15 minutes later.

RESULTS

The compounds of this invention administrered at doses from 50 pg/Kg i.v. to 0.2 mg/Kg i.v. shifted to the right the three-point dose-response curve to angiotensin I but did not change the dose-response curve to angiotensin II.

It may thus be concluded from the pressure figures that the compounds of formula I are without effect against angiotensin II but are efficient to curb the effects of angiotensin I by inhibiting its conversion into angiotensin II.

ANITE TOXICITY

The compounds of formula I administrered either intravenously or orally to mice are practically devoid of toxicity-$N_o$ death has been obtained.

What we claim is:

1. A compound of the formula

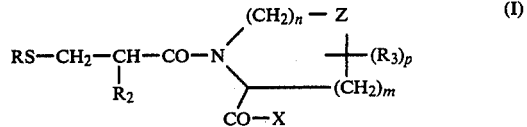

where
R is hydrogen, loweralkyl, loweralkanoyl, phenyl-loweralkyl or phenyl, where each of such phenyl rings may be substituted with one to three substituents selected from the group consisting of halogen, trifluoromethyl, lower alkyloxy, vinyl, lower alkylenedioxy, hydroxy and lower alkyl;
$R_2$ is hydrogen, loweralkyl or lower cycloalkyl;
Z is sulfur, sulfoxide or sulfonyl;
$R_3$ is hydrogen or loweralkyl;
m is 1;
n is 1;
p is 0, 1, or 2; and
X is an amino group.

2. The salts of the compounds of formula I according to claim 1 with an organic or inorganic base.

3. The diastereisomers and the optically active isomers of a compound according to claim 1.

4. A compound according to claim 1 which is N-(3 mercapto 2-methyl propionyl) thiazolidinyl-4-carboxamide.

5. The pharmaceutical compositions which includes as active ingredient (s) at least one compound of claim 1 or a base-addition salt thereof in admixture or conjunction with an inert non-toxic pharmaceutically-acceptable carrier or vehicle.

6. A pharmaceutical composition according to claim 5 in which the amount of a compound of claim 1 ranges from 10 to 100 mg per unit dosage.

7. A method for treating hypertension in hypertensive patients suffering from an excessive blood content of Angiotensin II which consists in administering to said patients a small but effective amount of a compound of claim 1 or a salt thereof to curb the conversion of Angiotensin I into Angiotensin II.

8. The method of claim 7 wherein the small but effective amount of a compound of claim 1 or a salt thereof ranges from 20 to 100 mg a day in the man.

* * * * *